United States Patent [19]

Singh et al.

[11] Patent Number: 4,761,744
[45] Date of Patent: Aug. 2, 1988

[54] METHOD AND DEVICE FOR DETERMINING HEATS OF COMBUSTION OF GASEOUS HYDROCARBONS

[75] Inventors: Jag J. Singh, Yorktown; Danny R. Sprinkle, Newport News; Richard L. Puster, Hampton, all of Va.

[73] Assignee: The United States of America as represented by the Administrator of the National Aeronautics and Space Administration, Washington, D.C.

[21] Appl. No.: 933,962

[22] Filed: Nov. 24, 1986

[51] Int. Cl.⁴ .................... G06F 15/46; G01N 25/22
[52] U.S. Cl. .................... 364/500; 236/15 E; 364/557; 364/571; 374/36; 431/13; 431/76
[58] Field of Search ............ 431/9, 115, 13, 76; 374/36, 37; 364/500, 557, 571; 236/15 E

[56] References Cited

U.S. PATENT DOCUMENTS

| | | | |
|---|---|---|---|
| 2,743,609 | 5/1956 | Schuller | 374/36 |
| 4,329,873 | 5/1982 | Maeda | 374/37 |
| 4,337,654 | 7/1982 | Austin et al. | 374/37 |
| 4,359,284 | 11/1982 | Kude et al. | 374/37 |
| 4,362,499 | 12/1982 | Nethery | 431/76 |
| 4,386,858 | 6/1983 | Kude et al. | 374/37 |
| 4,433,922 | 2/1984 | Bohl et al. | 374/36 |
| 4,492,559 | 1/1985 | Pocock | 431/76 |
| 4,500,214 | 2/1985 | Calvet et al. | 374/36 |
| 4,511,262 | 4/1985 | Arcara | 374/36 |
| 4,565,788 | 1/1986 | Milovidov et al. | 374/37 |
| 4,576,570 | 3/1986 | Adams et al. | 236/15 E |

Primary Examiner—Parshotam S. Lall
Assistant Examiner—Kevin J. Teska
Attorney, Agent, or Firm—George F. Helfrich; John R. Manning; Charles E. B. Glenn

[57] ABSTRACT

A method and device 15 is provided for a quick, accurate and on-line determination of heats of combustion of gaseous hydrocarbons. First, the amount of oxygen in the carrier stream air is sensed by oxygen sensing system 20. Second, three individual volumetric flow rates of oxygen, carrier stream air, and hydrocarbon test gas are introduced into burner 19. The hydrocarbon test gas is fed into burner 19 at a volumetric flow rate n measured by flowmeter 18. Third, the amount of oxygen in the resulting combustion products is sensed by oxygen sensing system 20. Fourth, the volumetric flow rate of oxygen is adjusted until the amount of oxygen in the combustion product equals the amount of oxygen previously sensed in the carrier stream air. This equalizing volumetric flow rate is m and is measured by flowmeter 16. The heat of combustion of the hydrocarbon test gas is then determined from the ratio m/n.

2 Claims, 4 Drawing Sheets

METHOD AND DEVICE FOR DETERMINING HEATS OF COMBUSTION OF GASEOUS HYDROCARBONS

ORIGIN OF THE INVENTION

The invention described herein was made by employees of the U.S. Government and may be manufactured and used by or for the Government for governmental purposes without the payment of any royalties thereon or therefor.

TECHNICAL FIELD OF THE INVENTION

This invention relates generally to calorimeters and more specifically to a method and device for determining heats of combustion of gaseous hydrocarbons.

BACKGROUND OF THE INVENTION

An accurate determination of the heats of combustion of various hydrocarbons is necessary in a variety of applications. For example, the production of simulated test media in wind tunnels for hypersonic vehicle studies requires a knowledge of the hydrocarbon properties. Also, natural gas suppliers often mix gas supplies from different sources. Since these mixtures must meet minimum federally mandated Btu standards, a determination of the heat of combustion for the mixture is necessary. Currently, this determination occurs off-line in a laboratory.

Several methods are currently utilized to determine the heats of combustion for gaseous hydrocarbons. One method, known as water-flow calorimetry, transfers heat resulting from hydrocarbon combustion to water and then measures the resulting temperature rise of the water, which is proportional to the heat of combustion. Disadvantages of water-flow calorimetry include a lengthy response time due to the relatively high thermal resistance of water and inexact data due to heat losses to the surrounding environment. Another method involves catalytically burning air and hydrocarbon gas of known volumetric flow-rates and then measuring the amount of oxygen utilized by combustion. This measured amount of oxygen is proportional to the heat of combustion of the hydrocarbon gas. One disadvantage of this method is that some prior knowledge of the hydrocarbon gas is needed. First, the air used must have sufficient oxygenic content to completely oxidize the hydrocarbon gas, which necessitates some knowledge of the composition of the hydrocarbon gas. Second, some knowledge of the composition of the hydrocarbon gas is required to select the optimal catalyst.

Accordingly, it is an object of this invention to provide an accurate method and device for measuring the heats of combustion of hydrocarbon gases which requires no prior knowledge of the hydrogen gas.

It is a further object of this invention to provide an accurate method and device for measuring the heats of combustion of hydrocarbon gases which may be quickly performed.

It is a further object of this invention to provide an accurate method and device for measuring the heats of combustion of hydrocarbon gases which may be performed on-line.

It is a further object of this invention to provide an accurate method and device for measuring the heats of combustion of hydrocarbon gases which can also be used for a mixture of hydrocarbon gas and inert gases such as nitrogen and helium.

Other objects and advantages of this invention will become apparent hereinafter in the specification and drawings which follow.

SUMMARY OF THE INVENTION

According to the present invention, the foregoing and additional objects are obtained by measuring the ratio of m/n, where m is the volumetric flow rate of oxygen needed to enrich the carrier stream air in which the hydrocarbon test gas, flowing at the volumetric rate of n, is burnt such that the mole fraction of oxygen in the resulting combustion product gases equals that in the carrier stream air. This m/n value is directly related to the heats of combustion of the hydrocarbon test gas. First, the amount of oxygen in the carrier stream air is determined. Second, three individually controlled flows of carrier stream air, oxygen, and a hydrogen test gas are fed into a burner and result in combustion product gases. The hydrocarbon test gas is fed into the burner at a volumetric flow rate of n. Third, the amount of oxygen in the resulting combustion product is sensed. Fourth, the volumetric flow rate of oxygen flowing into the burning is adjusted until the amount of oxygen sensed in the resulting combustion product is equal to that previously sensed in the carrier stream air. The equalizing volumetric flow/rate of oxygen is m. The heat of combustion of the hydrocarbon test gas is then determined from the ratio m/n.

DETAILED DESCRIPTION OF THE INVENTION

Figure 1:
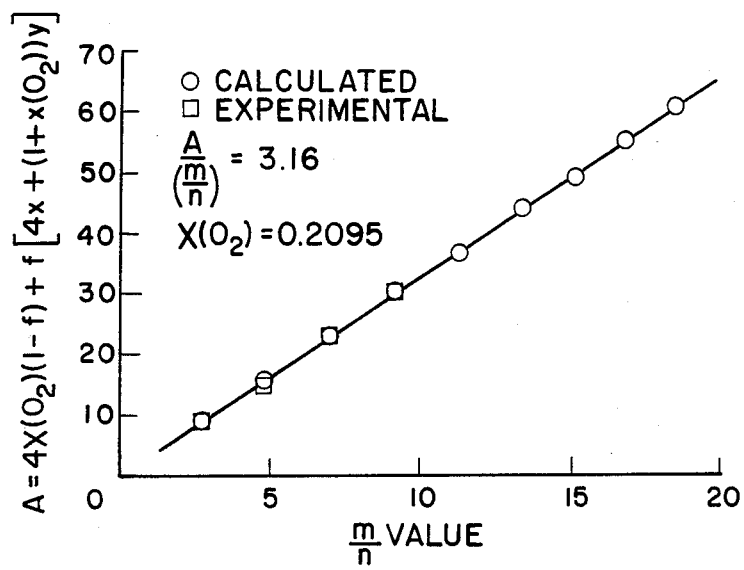
FIG. 1 is a graph showing the relationship of the heat of combustion constant A to m/n for pure saturated hydrocarbon gases.

A general expression for the combustion of a natural gas sample in oxygen enriched air can be written as follows:

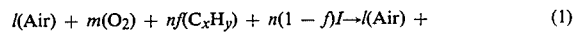

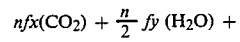

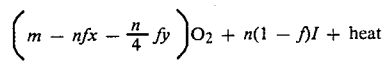

where
$(C_xH_y+I)$ = Test gas
$C_xH_y$ = Effective hydrocarbon in the test gas (for saturated hydrocarbons, $y = 2x+2$), I = Non-combustible impurities in test gas,
f = Combustible fraction of test gas,
l = Volumetric flow rate of carrier stream air,
m = Volumetric flow rate of oxygen, and
n = Volumetric flow rate of hydrocarbon test gas.

The mole fraction of oxygen in the products of equation (1) is:

$$X(O_2) = \frac{0.2095\,l + \left[m - \frac{nf}{4}(4x+y)\right]}{l + nfx + \frac{n}{2}fy + \left[m - \frac{nf}{4}(4x+y)\right] + n(1-f)} \quad (2)$$

$$= \frac{0.2095\,l + m - \frac{nf}{4}(4x+y)}{l + m + n + nf\left(\frac{y-4}{4}\right)}$$

where $X(O_2)$ = Mole fraction of oxygen in the combustion products.

If $X(O_2) = 0.2095$, we obtain:

$$\frac{0.838(1-f) + f(4x + 1.2095\,y)}{3.162} = \frac{m}{n} \quad (3)$$

If $f = 1$ (i.e., the test gas has *no* non-combustible impurities in it), equation (3) reduces to:

$$\frac{4x + 1.2095\,y}{3.162} = \frac{m}{n} \quad (3a)$$

If, on the other hand, $f = 0$ (i.e., no combustible fraction is present in the test gas), equation (3) reduces to:

$$0.2650 = \frac{m}{n} \quad (3b)$$

Generalizing equation (3) for non-standard air, we obtain:

$$\frac{4\,X(O_2)(1-f) + f[4x + (1 + X(O_2))\,y]}{4[1 - X(O_2)]} = \quad (4)$$

$$\frac{A}{4[1 - X(O_2)]} = \frac{m}{n}$$

A is a constant which obviously depends solely on the composition of the hydrocarbon test gas ($C_xH_y + I$) and the mole fraction of oxygen in the air used for combustion.

Figure 2:
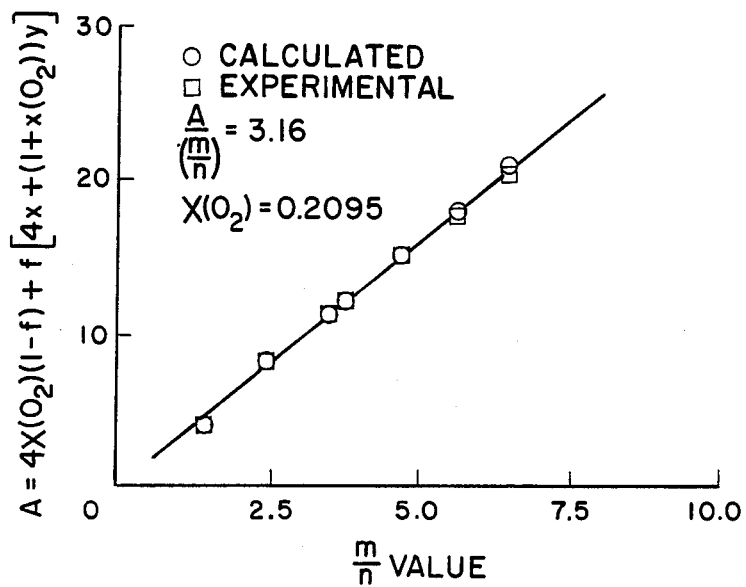
FIG. 2 is a graph showing the relationship of the heat of combustion constant A to m/n for a binary mixture of hydrocarbon gases.

Referring to FIG. 1, the correlation between A and m/n is shown. It is apparent that A and m/n are linearly related. If $f \neq 1$, m/n values for various impurity-containing hydrocarbon gases will be different from those for pure hydrocarbons. An experimental measurement of m/n will then give f, the combustible fraction in the test gas. Referring now to FIG. 2, the correlation between A and m/n for binary hydrocarbon gas mixtures is shown. FIGS. 1 and 2 clearly demonstrate that the m/n values for gases containing saturated hydrocarbons are uniquely related to their hydrogen and carbon contents.

Figure 3:
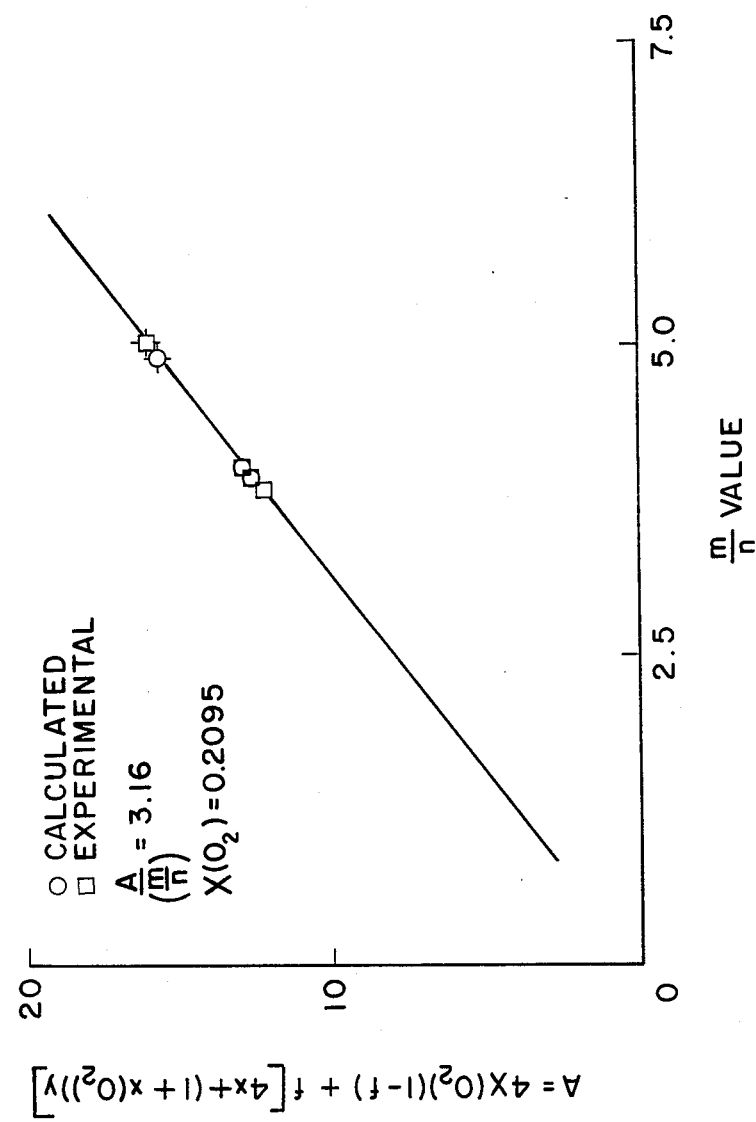
FIG. 3 is a graph showing the relationship of the heat of combustion constant A to m/n for a mixture of hydrocarbon and inert gases.

If the test gas is a mixture of two or more hydrocarbons, equation (4) can be used to readily calculate the m/n-value for the "effective" test hydrocarbon. For example, for a test gas containing equal mole fractions of $CH_4$ and $C_2H_6$, the effective equivalent hydrocarbon would be $C_{1.5}H_{5.0}$, giving m/n = 3.81 for $X(O_2) = 0.2095$. If this mixture also contained an incombustible impurity, the corresponding m/n-value would be lower, as indicated by equation (4). Referring now to FIG. 3, A is seen to be a function of m/n for f = 1 for test gases containing several saturated hydrocarbons as well as non-combustible gases. Again, the uniqueness of correlation between A and m/n is evident.

Because m/n-values for various test gases containing saturated hydrocarbons are related to their chemical composition, they can serve as the basis for direct determinations of their heats of combustion. Table I below summarizes the gross heats of combustion of several pure saturated hydrocarbons.

TABLE I

| Hydrocarbon | m/n $X(O_2) = 0.2095$ | Heat of Combustion (kcal/mol) | Heat of Combustion $\left[\frac{\text{(kcal/mol)}}{\text{m/n}}\right]$ |
|---|---|---|---|
| $CH_4$ | 2.795 | 212.80 | 76.14 |
| $C_2H_6$ | 4.825 | 372.82 | 77.27 |
| $C_3H_8$ | 6.855 | 530.61 | 77.40 |
| $C_4H_{10}$ | 8.885 | 687.65 | 77.39 |
| $C_5H_{12}$ | 10.915 | 845.10 | 77.43 |
| $C_6H_{14}$ | 12.945 | 1002.55 | 77.45 |

Figure 4:
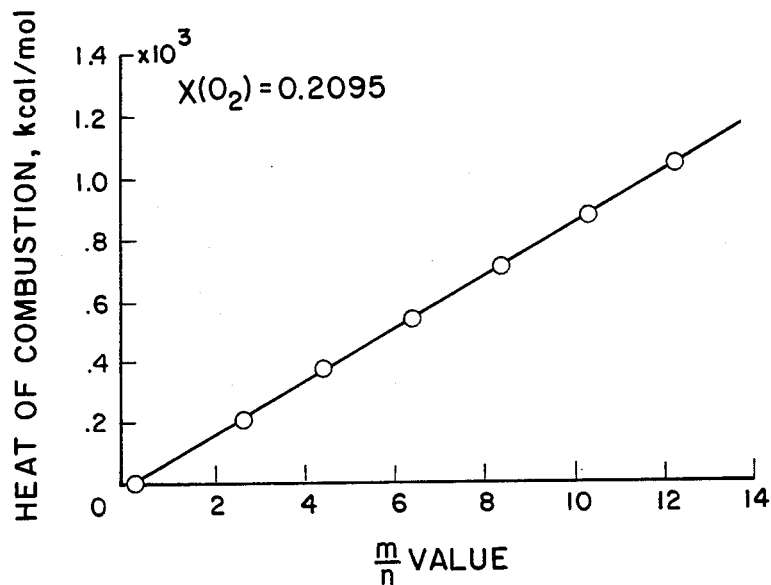
FIG. 4 is a graph showing the relationship of the heat of combustion to m/n for several hydrocarbon gases.
Figure 5:
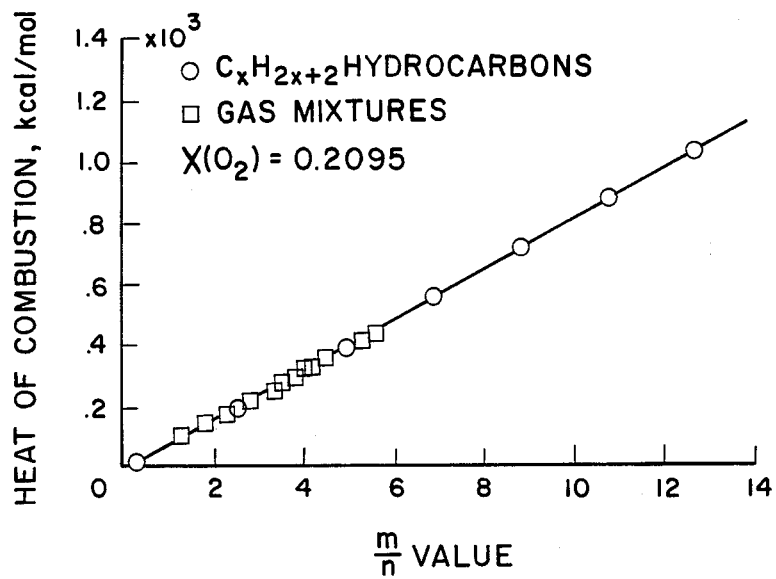
FIG. 5 is a graph showing the relationship of the heat of combustion to m/n for several mixtures of saturated hydrocarbon and inert gases.

Referring now to FIG. 4, the heats of combustion (kcal/mol) vs. m/n values for several selected hydrocarbons are shown. Referring now to FIG. 5, the heats of combustion vs. m/n values for mixtures containing selected saturated hydrocarbons and non-combustible gases is shown. It is apparent that the heats of combustion of various gases are directly related to their corresponding m/n values. Therefore, determination of m/n for the hydrocarbon test gas provides an on-line determination of its heat of combustion.

Referring to Table I and equation 3(b), the following relationship between heats of combustion and m/n has been derived:

$$\Delta H° = A_0 + A_1(m/n) + A_2(m/n)^2 + A_3(m/n)^3 + A_4(m/n)^4 \quad (5)$$

where
$\Delta H°$ = heat of combustion (kcal/mol),
$A_0 = -23.5580$,
$A_1 = 89.5119$,
$A_2 = -2.2580$,
$A_3 = 0.1795$, and
$A_4 = -0.0051$.

Constants $A_0 \rightarrow A_4$ were determined using a least squares fit to a fourth power equation expressing $\Delta H°$ as a function of m/n.

Figure 6:
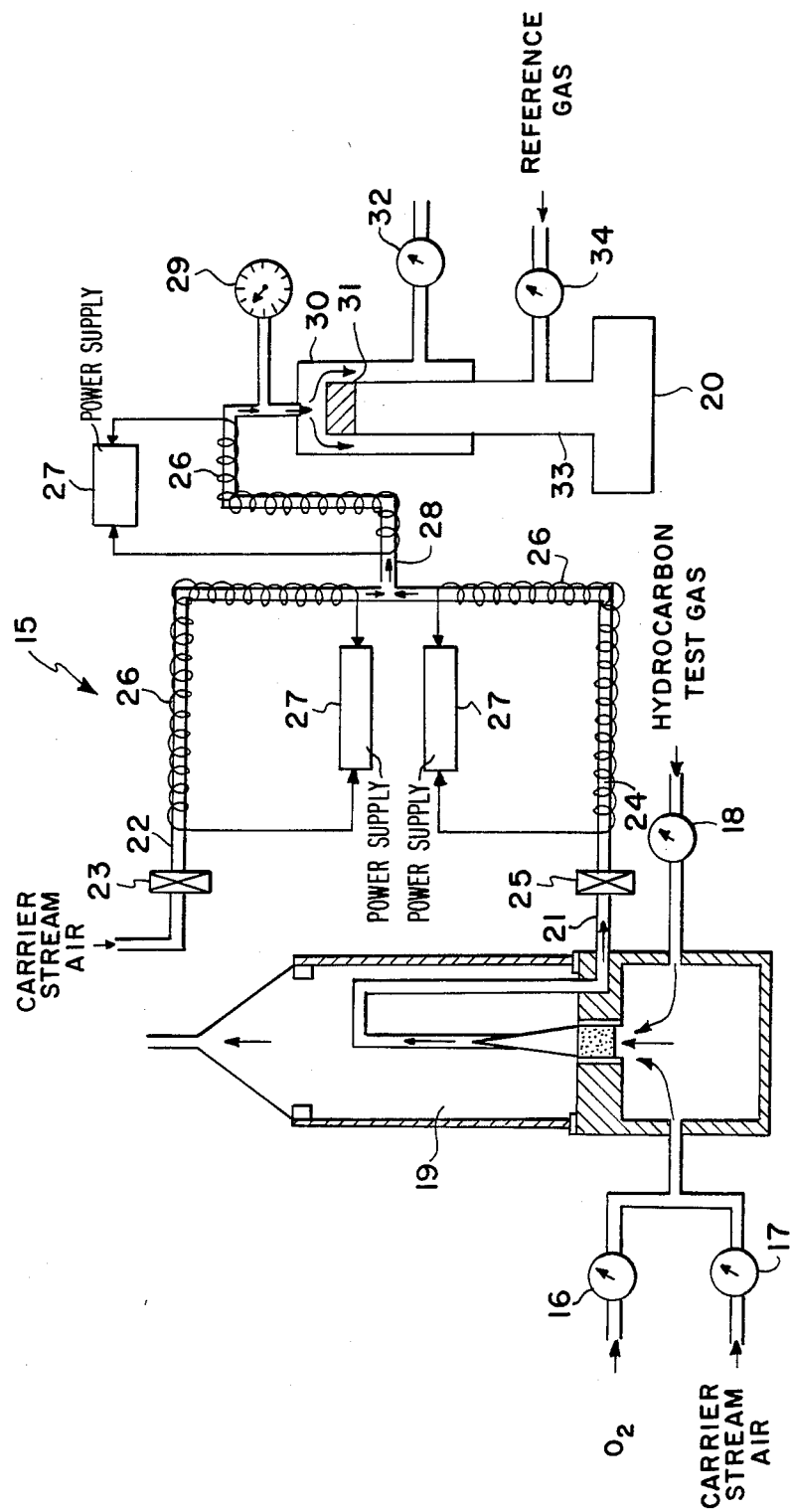
FIG. 6 is a schematic diagram of the device for determining heats of combustion of hydrocarbon test gases.

As illustrated in FIG. 6, a device 15 for determining heats of combustion of various hydrocarbon test gases is comprised of an oxygen flow meter 16, a carrier stream air flow meter 17, a hydrocarbon test gas flow meter 18, a burner 19, and an oxygen sensing system 20. First, carrier stream air is directed through air valve 23 and air conduit 22 to one end of main sensor conduit 28. Both air conduit 22 and main sensor conduit 28 are wrapped with heater tape 26, which is controlled by a variable AC voltage source 27 to ensure a temperature sufficient to avoid condensation of the gases in the conduits.

The other end of main sensor conduit 28 connects to sensor chamber 30. Sensor chamber 30 contains oxygen sensor disc 31. A pump (not shown) is connected to sensor chamber 30 via a pump flow meter 32. This pump allows sample gas to flow through main sensor conduit 28 and to come in contact with one side oxygen sensor disc 31. This oxygen sensor disc 31 is connected to oxygen sensing system 20 and reference gas chamber 33. A reference gas, standard air, is fed at constant volumetric flow rate by flowmeter 34 into reference gas chamber 33 and into contact with the other side of oxygen sensor disc 31. An electrical potential is developed across oxygen sensor disc 31 from the sample gas on one side and the reference gas on the other. This electrical potential is read by oxygen sensing system 20 and is proportional to the amount of oxygen in the sample gas. Accordingly, the amount of oxygen present in the carrier stream air is determined.

Next, air valve 23 is closed and sample gas valve 25 is opened. Sample gas valve 25 connects one end of sample gas conduit 24 to one end of burner conduit 21. Sample gas conduit 24 is also wrapped with heater tape 26, which is controlled by a variable AC voltage source 27 to ensure a temperature sufficient to avoid condensation of the combustion products in sample gas conduit 24. The other end of sample gas conduit 24 connects to main sensor conduit 28.

The other end of sample gas conduit receives combustion products from burner 19. Hydrocarbon test gas is fed into burner 19 at a volumetric flow rate n controlled by hydrocarbon test gas flowmeter 18. Carrier stream air is fed into burner 19 at a constant volumetric flow rate controlled by carrier stream flowmeter 17. Oxygen is fed into burner 19 at a volumetric flow rate controlled by oxygen flowmeter 16. Initially, oxygen flowmeter 16 is closed. The resulting combustion products travel through burner conduit 21 and ultimately contact one side of oxygen sensor disc 31. A pressure gauge 29 is connected to main sensor conduit 28 to ensure that the previously sensed carrier stream air and the combustion products contact oxygen sensor disc 31 with the same pressure. Incorrect data can result if the pressure varies in sensor chamber 30.

Once the resulting combustion products contact one side of oxygen sensor disc 31, the amount of oxygen present in the combustion products is sensed by oxygen sensing system 20 in the manner described above. Oxygen flowmeter 16 is gradually opened until the amount of oxygen present in the combustion products equals the amount of oxygen previously sensed in the carrier stream air. This equalizing volumetric flow rate of oxygen is m.

The heat of combustion is then quickly determined using both the volumetric flow rate n recorded by hydrocarbon test gas flowmeter 18 and this equalizing volumetric flow rate m in equation (5).

What is claimed is:

1. A method of determining the heat of combustion of a hydrocarbon test gas comprising:

provinding a flow of carrier stream air containing oxygen;

sensing the amount of oxygen in said flow of carrier stream air;

introducing three individual volumetric flow rates of carrier stream air, oxygen, and hydrocarbon test gas into a burner to produce combustion products containing oxygen;

sensing the amount of oxygen in said combustion products;

adjusting said flow of oxygen until the amount of oxygen in said combustion products is equal to the previously sensed amount of oxygen in the carrier stream air; and calculating the heat of combustion of said hydrocarbon test gas from the following equation:

$$\Delta H° = A_0 + A_1(m/n) + A_2(m/n)^2 + A_3(m/n)^3 + A_4(m/n)^4$$

where, $\Delta H°$ is the heat of combustion of said hydrocarbon test gas, m is the volumetric flow rate of said individual flow of oxygen which equalizes the amount of oxygen in said combustion products with the previously sensed amount of oxygen in the carrier stream air, n is the volumetric flow rate said individual flow of hydrocarbon test gas which is introduced into the burner, and $A_0$, $A_1$, $A_2$, $A_3$ and $A_4$ are constants determined by using a least squares fit to a fourth power equation expressing $\Delta H°$ as a function of m/n.

2. A device for determining the heat of combustion of a hydrocarbon test gas comprising:

a means for providing a flow of carrier stream air containing oxygen;

a means for sensing the amount of oxygen in said flow of carrier stream air;

a means for introducing three individual volumetric flow rates of carrier stream air, oxygen, and hydrocarbon test gas into a burner to produce combustion products containing oxygen;

a means for sensing the amount of oxygen in said combustion products;

a means for adjusting said individual flow of oxygen until the amount of oxygen in said combustion products is equal to the previously sensed amount of oxygen in the carrier stream air; and a means for calculating the heat of combustion of said hydrocarbon test gas from the following equation:

$$\Delta H° = A_0 + A_1(m/n) + A_2(m/n)^2 + A_3(m/n)^3 + A_4(m/n)^4$$

where, $\Delta H°$ is the heat of combustion of said hydrocarbon test gas, m is the volumetric flow rate of said individual flow of oxygen which equalizes the amount of oxygen in said combustion products with the amount of oxygen in the carrier stream air, n is the volumetric flow rate said individual flow of hydrocarbon test gas, and $A_0$, $A_1$, $A_2$, $A_3$ and $A_4$ are constants determined by using a least squares fit to a fourth power equation expressing $\Delta H°$ as a function of m/n.

* * * * *